US00PP31243P2

(12) United States Plant Patent
Zhou et al.

(10) Patent No.: US PP31,243 P2
(45) Date of Patent: Dec. 17, 2019

(54) ***NELUMBO* PLANT NAMED 'FU FEN'**

(50) Latin Name: *Nelumbo nucifera*
Varietal Denomination: Fu Fen

(71) Applicants: Shirong Zhou, Hangzhou (CN); Xianbao Zeng, Hangzhou (CN)

(72) Inventors: Shirong Zhou, Hangzhou (CN); Xianbao Zeng, Hangzhou (CN)

(73) Assignee: Zhejiang Renwen Laudscape Architecture Co., Ltd., Hangshou (CN)

( * ) Notice: Subject to any disclaimer, the term of this patent is extended or adjusted under 35 U.S.C. 154(b) by 0 days.

(21) Appl. No.: 16/350,035

(22) Filed: Sep. 17, 2018

(51) Int. Cl.
*A01H 5/02* (2018.01)

(52) U.S. Cl.
USPC ..... Plt./342

(58) Field of Classification Search
USPC ..... Plt./342
CPC ..... A01H 5/00; A01H 5/02; A01H 6/00
See application file for complete search history.

*Primary Examiner* — Keith O. Robinson
(74) *Attorney, Agent, or Firm* — C. A. Whealy

(57) ABSTRACT

A new and distinct cultivar of *Nelumbo* plant named 'Fu Fen', characterized by its upright plant habit; moderately vigorous growth habit; large medium green-colored leaves; freely flowering habit; and large light red purple-colored bowl-shaped flowers that are positioned above the foliar plane on moderately strong and erect peduncles.

2 Drawing Sheets

Botanical designation: *Nelumbo nucifera.*
Cultivar denomination: 'FU FEN'.

BACKGROUND OF THE INVENTION

The present invention relates to a new and distinct cultivar of *Nelumbo* plant, botanically known as *Nelumbo nucifera*, commonly referred to as Sacred or Indian Lotus, and hereinafter referred to by the name 'Fu Fen'.

The new *Nelumbo* plant is a product of a controlled breeding program conducted by the Inventors in Hangzhou, Zhejiang, China. The objective of the breeding program is to create new *Nelumbo* plants that have attractive and unique flower forms and flower colors.

The new *Nelumbo* plant originated from a cross-pollination in July, 2013 of *Nelumbo nucifera* 'Da Sajin', not patented, as the female, or seed, parent with *Nelumbo nucifera* 'Dong Honghua', not patented, as the male, or pollen, parent. The new *Nelumbo* plant was discovered and selected by the Inventors as a single flowering plant within the progeny of the stated open-pollination in a controlled greenhouse environment in Hangzhou, Zhejiang, China in July, 2015.

Asexual reproduction of the new *Nelumbo* plant by rhizome divisions in a controlled environment in Hangzhou, Zhejiang, China since April, 2017 has shown that the unique features of this new *Nelumbo* plant are stable and reproduced true to type in successive generations of asexual reproduction.

SUMMARY OF THE INVENTION

Plants of the new *Nelumbo* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fu Fen'. These characteristics in combination distinguish 'Fu Fen' as a new and distinct *Nelumbo* plant:

1. Upright plant habit.
2. Moderately vigorous growth habit.
3. Large medium green-colored leaves.
4. Freely flowering habit.
5. Large light red purple-colored bowl-shaped flowers that are positioned above the foliar plane on moderately strong and erect peduncles.

Plants of the new *Nelumbo* differ from plants of the female parent, 'Da Sajin', in the following characteristics:

1. Flowers of plants of the new *Nelumbo* have more petals than flowers of plants of 'Da Sajin'.
2. Flowers of plants of the new *Nelumbo* have light red purple-colored petals and petaloids whereas petals and petaloids of flowers of plants of 'Da Sajin' are white and red bi-colored.

Plants of the new *Nelumbo* differ from plants of the male parent, 'Dong Honghua', in the following characteristics:

1. Flowers of plants of the new *Nelumbo* are double-type bowl-shaped whereas flowers of plants of 'Dong Honghua' are single-type cup-shaped.
2. Flowers of plants of the new *Nelumbo* are darker red purple in color than flowers of plants of 'Dong Honghua'.

Plants of the new *Nelumbo* can be compared to plants of *Nelumbo nucifera* 'Fen Mudan', not patented. In side-by-side comparisons plants of the new *Nelumbo* differ primarily from plants of 'Fen Mudan' in the flower color as plants of the new *Nelumbo* have light red purple-colored flowers whereas plants of 'Fen Mudan' have light yellow orange-colored flowers.

BRIEF DESCRIPTION OF THE PHOTOGRAPHS

The accompanying photographs illustrate the overall appearance of the new *Nelumbo* plant showing the colors as true as it is reasonably possible to obtain in colored reproductions of this type. Colors in the photographs may differ slightly from the color values cited in the detailed botanical description which accurately describe the colors of the new *Nelumbo* plant. The photograph on the first sheet is a side perspective view of a typical plant of 'Fu Fen' grown in a container. The photograph on the second sheet is a close-up view of a typical flower of 'Fu Fen'.

DETAILED BOTANICAL DESCRIPTION

The aforementioned photographs and following observations and measurements describe plants grown during the summer in 50-cm by 35-cm containers in an outdoor nursery in Hangzhou, Zhejiang, China and under cultural practices typical of commercial *Nelumbo* production. During the production of the plants, day temperatures ranged from 14° C. to 33° C. and night temperatures ranged from 16° C. to 28° C. Plants were one year old when the photographs and the detailed description were taken. In the following description, color references are made to The Royal Horticultural Society Colour Chart, 2007 Edition, except where general terms of ordinary dictionary significance are used.

Botanical Classification: *Nelumbo nucifera* 'Fu Fen'.

Parentage:

*Female, or seed, parent.*—*Nelumbo nucifera* 'Da Sajin', not patented.

*Male, or pollen, parent.*—*Nelumbo nucifera* 'Dong Honghua', not patented.

Propagation:

*Type.*—By rhizome divisions.

*Time to initiate roots, summer.*—About four days at temperatures about 27° C.

*Time to produce a rooted young plant.*—About six days at temperatures about 27° C.

*Root description.*—Fine, fleshy; typically white to grey brown in color, actual color of the roots is dependent on water quality, fertilizer type and formulation, substrate temperature and physiological age of roots.

*Rooting habit.*—Not freely branching, medium density.

Plant Description:

*Plant and growth habit.*—Upright plant habit; moderately vigorous growth habit and moderate growth rate.

*Plant height* (*soil level to top of foliar plane*).—About 80 cm.

*Plant height* (*soil level to top of floral plane*).—About 85 cm.

*Plant diameter.*—About 140 cm by 110 cm.

Rhizome Description:

*Arrangement and habit.*—Sympodial branching habit with about 10 to 15 primary branches developing per plant each with about five to eight secondary branches.

*Length.*—About 110 cm to 160 cm.

*Diameter.*—About 1.3 cm to 6.2 cm.

*Internode length.*—About 8 cm to 34 cm.

*Texture and luster.*—Smooth, glabrous; glossy.

*Color.*—White, close to NN155A.

Leaf Description:

*Length, fully expanded.*—About 27 cm to 33 cm.

*Width, fully expanded.*—About 22 cm to 30 cm.

*Shape.*—Peltate, elliptical.

*Apex.*—Retuse.

*Base.*—Cuneate.

*Margin.*—Entire; undulate.

*Venation.*—Palmate.

*Texture and luster, upper and lower surfaces.*—Pubescent, papery; moderately glossy.

*Color.*—Developing leaves, upper surface: Close to 143B. Developing leaves, lower surface: Close to 147C. Fully expanded leaves, upper surface: Close to 139A; venation, close to 139C. Fully expanded leaves, lower surface: Close to 148D; venation, close to 139D.

*Petioles.*—Length: About 70 cm. Diameter: About 4 mm to 8 mm. Strength: Moderately strong. Texture and luster, upper and lower surfaces: Smooth, glabrous; moderately glossy. Color: Close to 138B.

Inflorescence Description:

*Arrangement.*—Double-type bowl-shaped flowers developing directly from the rhizomes with numerous showy petals and petaloids; about 13 flower buds and flowers developing per plant at one time.

*Time to flower.*—In China, plants flower from June to August; flowering continuous during this period; flowers begin opening at 05:00 hours in the morning, flowers are fully opened at about 06:30 hours and are typically closed by 09:00 hours.

*Flower longevity.*—Flowers last about five days on the plant; flowers last about three days as a cut flower; flowers persistent; plants maintain good substance for about 40 days.

*Fragrance.*—Initially, very faint and then not detectable.

*Flower buds.*—Length: About 8 cm. Diameter: About 5 cm. Shape: Ovate. Texture and luster: Smooth, glabrous; matte. Color: Close to 67A.

*Flowers.*—Shape and arrangement: Double-type, bowl-shaped with numerous showy petals and petaloids. Diameter: About 21 cm. Height: About 10 cm.

*Petals.*—Quantity and arrangement: About 118 arranged in numerous whorls. Length: About 9.8 cm. Width: About 6.7 cm. Shape: Obovate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening and fully opened, upper surface: Distally, close to 73A; mid-section and towards the base, close to 75C; at the base, close to 2D; venation, similar to lamina colors, close to 73A, 75C and 2D; color becoming closer to 75D with development. When opening and fully opened, lower surface: Distally, close to 73A; mid-section and towards the base, close to 75C; at the base, close to 2D; venation, close to 75C; color becoming closer to 75D with development.

*Petaloids.*—Quantity and arrangement: About 99 arranged in numerous whorls. Length: About 5.1 cm. Width: About 1.1 cm. Shape: Oblanceolate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening and fully opened, upper surface: Distally, close to 73A; mid-section and towards the base, close to 75C; at the base, close to 2D; venation, similar to lamina colors, close to 73A, 75C and 2D; color becoming closer to 75D with development. When opening and fully opened, lower surface: Distally, close to 73A; mid-section and towards the base, close to 75C; at the base, close to 2D; venation, close to 75C; color becoming closer to 75D with development.

*Sepals.*—Quantity and arrangement: About four in a single whorl. Length: About 6.8 cm. Width: About 5.8 cm. Shape: Obovate. Apex: Acuminate. Base: Cuneate. Texture and luster, upper and lower surfaces: Smooth, glabrous; moderately glossy. Color: When opening, upper and lower surfaces: Close to 76C. Fully opened, upper surface: Close to 76B. Fully opened, lower surface: Close to 76C.

*Peduncles.*—Length: About 115 cm. Diameter: About 1.3 cm to 2.3 cm. Strength: Moderately strong. Aspect: Mostly erect. Texture and luster: Smooth, glabrous; slightly glossy. Color: Close to 145A.

*Stamens.*—Quantity per flower: About 95. Filament length: About 2.2 cm. Filament color: Close to 4C. Anther length: About 1.3 cm. Anther width: About 1 mm. Anther shape: Lanceolate. Anther color: Close to 6C. Pollen amount: Moderate. Pollen color: Close to 6C.

*Pistils.*—Quantity per flower: About 14. Pistil length: About 3.9 cm. Style length: About 2.4 cm. Style color: Close to 5A. Stigma diameter: About 1 mm. Stigma shape: Rounded. Stigma color: Close to 6A. Ovary color: Close to 5A.

*Fruits.*—Quantity per plant: About 19. Length: About 4.7 cm. Diameter: About 12 cm. Texture: Smooth, glabrous. Color: Close to 138A.

*Seeds.*—Quantity per fruit: About six to eleven. Length: About 2.9 cm. Diameter: About 1.7 cm. Texture: Smooth, glabrous. Color: Close to N200B.

Pathogen & Pest Resistance: To date, plants of the new *Nelumbo* have not been observed to be resistant to pathogens or pests common to *Nelumbo* plants.

Temperature Tolerance: Plants of the new *Nelumbo* have been observed to be tolerant to temperatures ranging from about −5° C. to about 40° C.

It is claimed:

1. A new and distinct *Nelumbo* plant named 'Fu Fen' as illustrated and described.

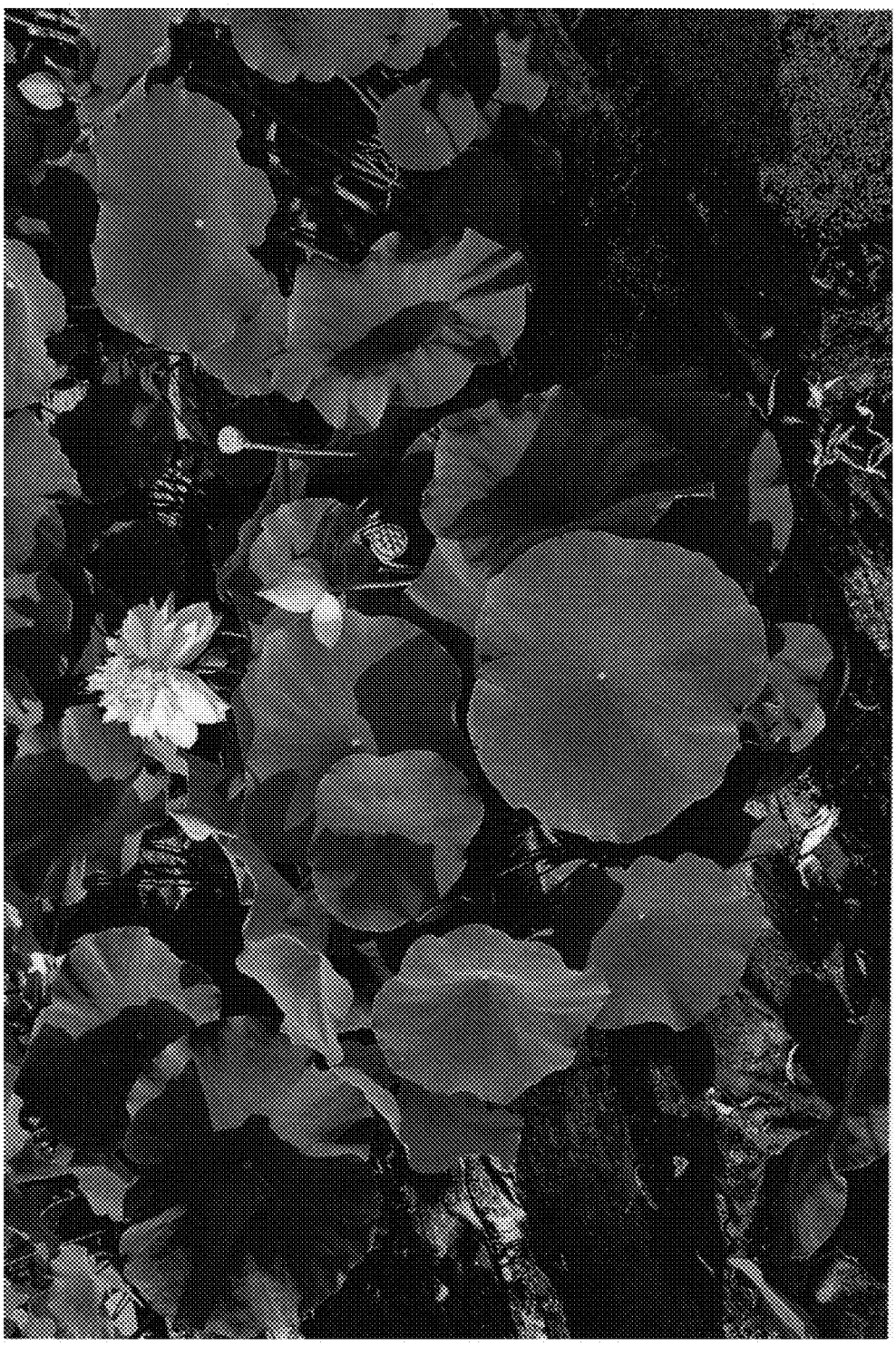

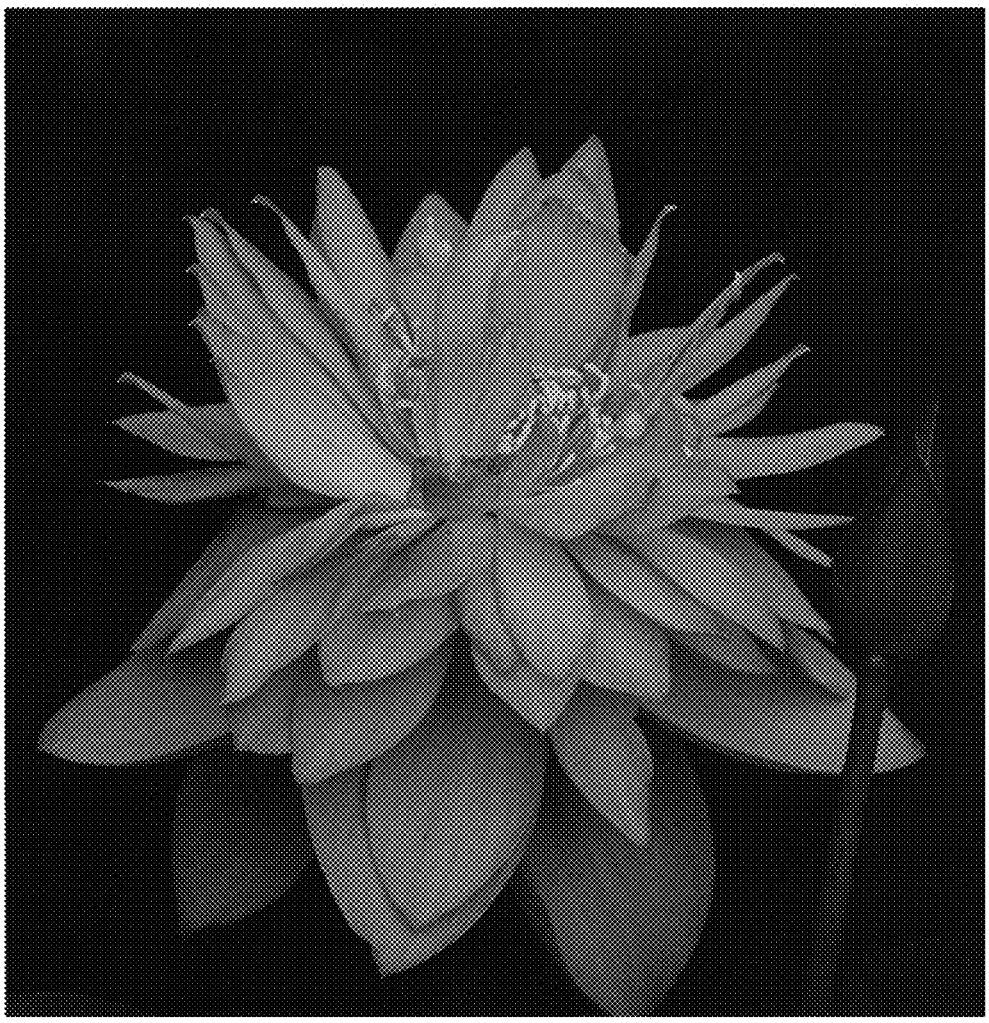

* * * * *